United States Patent [19]

Moreau et al.

[11] Patent Number: 4,606,741
[45] Date of Patent: Aug. 19, 1986

[54] PROCESS FOR PURIFYING NATURAL GAS

[75] Inventors: Claude J. Moreau, Chaville; Joseph Y. Larue, Chambourcy; Alexandre Rojey, Garches, all of France

[73] Assignees: Compagnie Francaise des Petroles; Institut Francais du Petrole, both of France

[21] Appl. No.: 763,896

[22] Filed: Aug. 9, 1985

Related U.S. Application Data

[63] Continuation of Ser. No. 640,919, Aug. 14, 1984, abandoned.

[30] Foreign Application Priority Data

Aug. 26, 1983 [FR] France ................. 83 13767

[51] Int. Cl.⁴ ............................................. B01D 59/10
[52] U.S. Cl. .......................................... 55/16; 55/32; 55/68; 55/73; 62/17; 62/24
[58] Field of Search ............... 55/16, 32, 40, 43, 68, 55/70, 73; 62/17, 20, 23, 24

[56] References Cited

U.S. PATENT DOCUMENTS

| | | | |
|---|---|---|---|
| 3,416,324 | 12/1968 | Swearingen | 62/23 |
| 3,886,757 | 6/1975 | McClintock et al. | 62/20 |
| 3,899,312 | 8/1975 | Kruis et al. | 62/17 |
| 4,130,403 | 12/1978 | Cooley et al. | 55/16 |
| 4,475,347 | 10/1984 | Hegarty et al. | 62/17 |

Primary Examiner—Charles Hart
Attorney, Agent, or Firm—Sughrue, Mion, Zinn, Macpeak, and Seas

[57] ABSTRACT

In a process for purifying natural gas in which methanol is injected into the natural gas, the temperature of the mixture of natural gas and methanol is lowered to the absorption temperature, at which undesirable components present in the natural gas are absorbed by the methanol, and the natural gas thus purified is separated from the methanol, the natural gas is subject to a succession of purification stages, each of which incorporates methanol injection into the natural gas, circulation of the mixture at the absorption temperature, and separation of the natural gas from the methanol phase. The partially purified natural gas which leaves a stage other than the last stage enters the stage which follows it and the purified natural gas is obtained at the outlet of the last stage. The methanol injected into the natural gas in any stage other than the last stage is the methanol separated at the outlet of the following stage, and at least a part of the spent methanol separated at the outlet of the first stage is regenerated by removing at least a part of the absorbed undesirable components and at least a part of the regenerated methanol is injected into the last stage.

5 Claims, 4 Drawing Figures

PROCESS FOR PURIFYING NATURAL GAS

This application is a continuation of Ser. No. 640,919, filed Aug. 14, 1984, now abandoned.

BACKGROUND OF THE INVENTION

The present invention relates to the purification of natural gas, particularly, but not exclusively, before its transport and/or its liquefaction.

Natural gas, whether in the form of gas combined with crude oil or dry gas, frequently contains, on leaving the production field, certain undesirable components such as water, carbon dioxide and hydrogen sulphide, at least a major part of which must be removed before certain operations such as, in particular, transport and/or liquefaction of the natural gas.

Numerous processes have already been proposed for purifying natural gas and more particularly for purification with solvents, but these processes require large installations such as absorption columns, which are costly and bulky, and incompatible with deep-sea exploitation or with offshore gas fields or deposits of oils and associated gas, both on account of the technical problems raised by the bulkiness and the exploitation, and of the economic problems.

The future development of the world gas production depends, among other factors, on the development of simpler and less costly processes for purifying the natural gas.

SUMMARY OF THE INVENTION

According to the invention there is provided a process for purifying natural gas, comprising injecting methanol into the natural gas, lowering the temperature of the mixture of natural gas and methanol thus produced to a temperature, called the absorption temperature, at which an absorption of undesirable components present in the natural gas by the methanol is produced, and separating the natural gas thus purified from the methanol phase which has absorbed the undesirable components, wherein the natural gas to be purified is subjected to a succession of purification stages, in each of which stages methanol is injected into the natural gas, the mixture of natural gas and methanol thus produced is subject to the absorption temperature, and the natural gas is separated from the methanol phase, the partially purified natural gas which leaves a stage other than the last stage enters the stage which follows it, purified natural gas being obtained at the outlet of the last stage, the methanol injected into the natural gas in any stage other than the last stage is the methanol separated at the outlet of the following stage, and at least a part of the methanol separated at the outlet of the first stage is regenerated by removing at least a part of the said undesirable components which it has absorbed and at least a part of the methanol regenerated in this way is injected into the last stage.

A counterflow effect can thus be obtained while in each stage there is a concurrent circulation of the methanol and the natural gas. The quantity of methanol which is employed can be reduced and the plant can be simplified.

Preferably, the temperature of the said separation of the natural gas from the methanol phase in any stage other than the first stage is lower than or equal to the temperature of the separation in the preceding stage, the temperature of the separation in the last stage is between $-30°$ and $-100°$ C. and the temperature of the separation in the first stage is below $10°$ C.

The natural gas to be purified may be subjected to a preliminary purification by permeation, upstream of the first stage of the said succession of purification stages. A preliminary purification by permeation in some cases makes it possible to reduce further the size of the multistage purification plant described above.

The methanol separated at the outlet of the first stage may be regenerated in two successive stages comprising a first stage for separating at least a part of the acid gases and a second stage for separating at least a part of the water. It is then advantageous to carry out an at least partial separation of the water only on a fraction of the total flow of spent methanol and this fraction is, preferably, less than 20%.

In addition, it has been found advantageous to inject methanol containing a weight proportion of water, which is between 5 and 50%, into the natural gas in the last stage.

Another subject of the invention consists in integrating the above described purification process with a process for liquefying natural gas by supplying the purified natural gas which leaves the last stage to a final heat exchanger which liquefies the natural gas by means of liquid nitrogen. The natural gas is preferably cooled by a stream of liquid nitrogen which enters the final heat exchanger and which then circulates from one stage to another in the said succession of purification stages in a direction opposite to that of the flow of the natural gas.

Embodiments according to the invention will now be described, by way of example only, with reference to the accompanying drawings.

DESCRIPTION OF THE PREFERRED EMBODIMENTS

Figure 1:
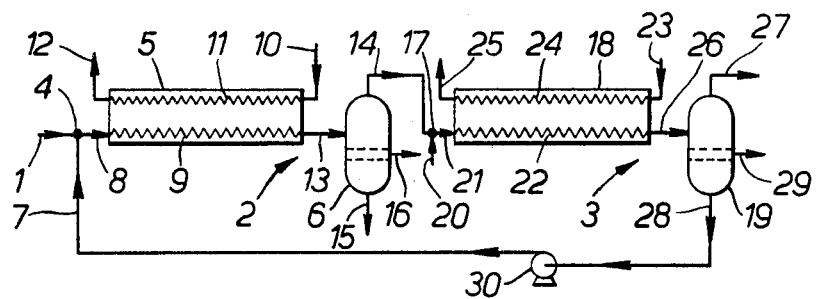
FIG. 1 shows diagrammatically an embodiment of a plant for purifying natural gas according to the present invention in two successive stages with more extensive cooling in the second stage.

As shown in FIG. 1, natural gas delivered by an inlet pipeline 1 is purified by being placed in contact with methanol, at a low temperature, in two successive purification stages 2 and 3.

Stage 2 incorporates, from upstream to downstream, a methanol injection point 4, a heat exchanger 5 and a separator vessel 6. Methanol is delivered by a methanol entry line 7 to the injection point 4, so that a mixture of natural gas and methanol flows, downstream of the injection point 4, along an inlet line 8 into the heat exchanger 5. This line 8 is connected to a passage 9 in the heat exchanger. A coolant fluid is delivered to the heat exchanger 5 via a line 10, flows in a passage 11, separate from passage 9, but in thermal contact with the latter, and leaves by a line 12.

During the cooling of the mixture of natural gas and methanol in the passage 9, a part of the undesirable components, such as water and the acid gases carbon dioxide and hydrogen sulphide, is absorbed by the methanol. The mixture of natural gas and methanol leaves the heat exchanger 5 via a line 13 and is delivered to the separator vessel 6 where the liquid and gaseous phases are separated and from which are withdrawn partially purified gas, from the upper part by a line 14, and spent methanol, from the lower part by a line 15. In some cases and depending on the composition of the natural gas to be purified, a quantity of hydrocarbons can sometimes condense during the cooling in the passage 9, which results in the appearance of a second liquid phase, which is separated in the vessel 6 and removed by a line 16.

Stage 3 incorporates, from upstream to downstream, a methanol injection point 17, a heat exchanger 18 and a separator vessel 19. The line 14 delivers partially purified gas, Methanol is delivered by line 20 to the injection point 17 where methanol is injected so that a mixture of natural gas and methanol flows downstream of the injection point 17 through an inlet line 21 into the heat exchanger 18. Line 21 is connected to a passage 22 in the heat exchanger 18. A coolant fluid is delivered to the heat exchanger 18 via a line 23, flows through a passage 24, separate from passage 22, but in thermal contact with the latter, and leaves by a line 25.

During the cooling of the mixture of natural gas and methanol in the passage 22, a major part of the undesirable components present in the natural gas is absorbed by the methanol. The mixture of natural gas and methanol leaves the heat exchanger 18 via a line 26 and is delivered to the separator vessel 19, where the liquid and gaseous phases separate and from which are extracted, purified gas, from the upper part by a line 27, and partially spent methanol, from the lower part by a line 28. If condensation of certain hydrocarbons takes place, a second liquid phase is separated in the vessel 19 and is removed by a line 29.

The partially spent methanol removed by the line 28 is the methanol which is injected into the natural gas circulation at the injection point 4. It is conveyed by a pump 30. At the injection point 17, new methanol is injected. This methanol is essentially, except for the small leaks which must be compensated by an outside supply, the methanol which is at least partially regenerated from the spent methanol leaving via the line 15.

The methanol regeneration plant arranged between the lines 15 and 20 is not shown in FIG. 1, because the methanol regeneration plant may be of a conventional type. It may, in particular, incorporate first a separation of at least a part of the acidic gases, which are light components, by pressure reduction and contact with an inert gas, and then a water separation. Water, being less volatile than methanol, is separated from it, for example by adsorption on a solid or by distillation.

The methanol injected into the line at the injection point 17 via the line 20 may still contain water, preferably in a weight proportion from 5% to 50%. Its absorbing properties and its freezing point are slightly modified thereby, but remain compatible with its use in the purification process described here. Moreover, in the case where cooling of the natural gas leads to condensation of liquid hydrocarbons, the presence of water in the methanol promotes the separation of these liquid hydrocarbons from the methanol, which reduces the losses of methanol in the liquid hydrocarbons and the entrainment of hydrocarbons with the methanol.

It is for this reason that provision may be made for carrying out at least a partial separation of methanol from water in respect of only a fraction of the total flow of recycled methanol, a fraction which is preferably less than 20%. The energy consumption is thus reduced while accumulation of water in the methanol during the operation of the natural gas purification plant is avoided.

Figure 2:
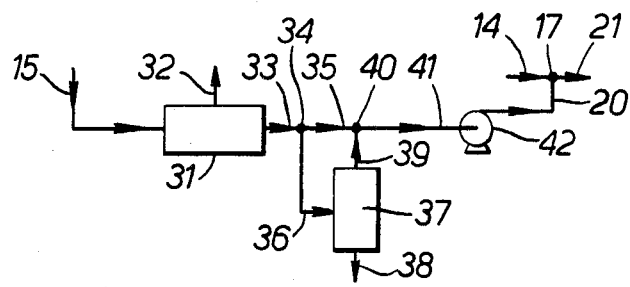
FIG. 2 shows diagrammatically an embodiment of a plant for regenerating the methanol.

FIG. 2 shows diagrammatically a methanol regeneration plant with separation of water from methanol carried out only on a branch of the main stream of methanol to be regenerated. The spent methanol leaving on line 15 and carrying various impurities such as water, carbon dioxide and hydrogen sulphide, first passes into a separator 31 for acid gases, in which its pressure is reduced to a pressure below that of the treated natural gas, and, if appropriate, is contacted with an inert carried gas. At least a part of the carbon dioxide and of the hydrogen sulphide is separated from the methanol and leaves the separator 31 via a line 32, while the methanol leaves via a line 33. At a Y-junction 34, the main part of the methanol flowing in the line 33 is directed via a line 35 towards the line 20 for introducing regenerated methanol into stage 3, while a minor proportion of the methanol is led via a line 36 to a water separator 37 which may be, for example, a distillation column. At least a part of the water is separated from the methanol and leaves a line 38, the methanol leaving via a line 39 to rejoin the main part of the methanol at a reinjection point 40. The total flow of the regenerated methanol thus obtained circulates in a line 41 under the action of a pump 42, to be reinjected into the natural gas at the injection point 17.

In the embodiment of FIG. 1, the natural gas to be purified, mixed with methanol, is cooled in stage 2 to a temperature which is intermediate the temperature in the entry pipeline 1 and the temperature in stage 3. For example, the cooling temperature in stage 2 is −60° C. and the cooling temperature in stage 3 is −80° C. It is also possible to carry out a complete cooling in stage 2 and merely to maintain stage 3 at the same temperature as that finally attained in stage 2. The final temperature of the natural gas/methanol mixture which is chosen is the lower, the higher the purification which is required in respect of the natural gas.

By splitting up the methanol purification system, into two or more stages, the consumption of methanol is reduced, because the absorption capacity of the latter is utilised better. The methanol consumption is the lower, the greater the number of stages.

Figure 3:
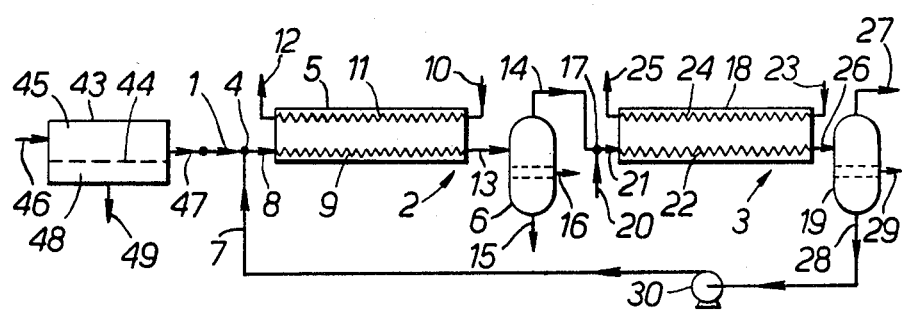
FIG. 3 shows diagrammatically an embodiment of a plant for purifying natural gas with methanol, such as that shown in FIG. 1, combined with a plant for purification by gas permeation.

The embodiment of FIG. 3 is similar to that of FIG. 1, except that, upstream of stage 2, a gaseous permeation separator 43 has been introduced, in which a membrane 44 divides an inner space into a supply enclosure 45, through which passes the main stream of natural gas between an inlet pipe 46 delivering the natural gas to be purified and an outlet line 47 connected to the pipe 1, undergoing a small pressure drop, and a permeation enclosure 48 which receives a secondary stream extracted from the total stream of natural gas by permeation through the membrane 44. This secondary stream is rich in components such as water, carbon dioxide and hydrogen sulphide. It leaves under a low pressure via a discharge line 49.

The addition of the permeation separator 43 is advantageous where the natural gas incorporates some concentration of undesirable components, because it makes it possible to reduce the rate of methanol circulation and the size of the heat exchangers 5 and 18. An optimum is to be sought in the purifying role which is assigned, respectively, to the gaseous permeation separator 43 and the methanol mixture absorption system.

The membrane 44 may be a cellulose acetate membrane for acid removal or carbon dioxide purification, at present commercially available. It is also possible advantageously to employ a membrane such as that recommended for use in French Patent Application No. 83/01,815 of Feb. 4, 1983 for: "Process for gas dehydration".

Figure 4:
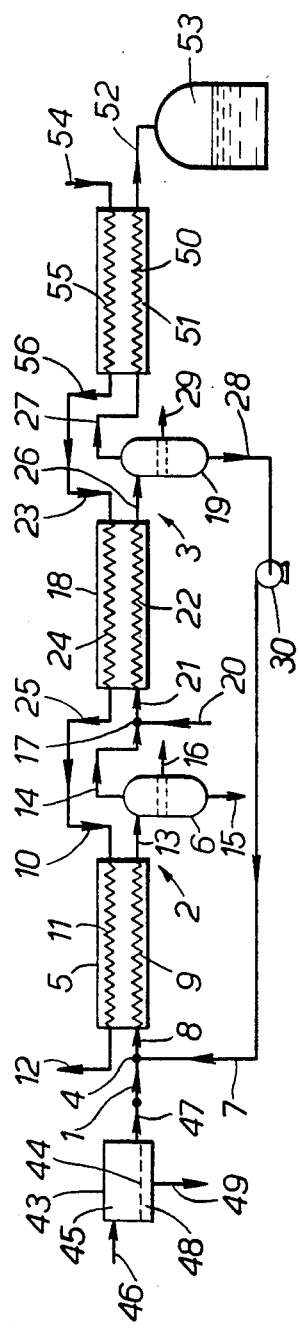
FIG. 4 shows diagrammatically an embodiment of a plant for liquefying natural gas incorporating a plant for purification of natural gas such as that shown in FIG. 3.

FIG. 4 shows diagrammatically a plant for purifying natural gas which is similar to that of FIG. 3, but to which has been added a supplementary plant for liquefying purified natural gas. An economical unit is thus obtained, with the purified natural gas being already at a low temperature at the outlet of the purification system, before its entry into the liquefying system.

The outlet line 27 for purified natural gas is connected to a passage 50 of a final heat exchanger 51, where the natural gas liquefies and from which it is conveyed by a line 52 to a storage tank 53. The final heat exchanger 51 is cooled by a coolant fluid entering via a line 54, circulating in a passage 55 and leaving via a line 56. This coolant fluid is preferably liquid nitrogen delivered at approximately $-195°$ C.

In the case where liquid nitrogen is employed as coolant in the purification plant it may be advantageous to connect the lines 56 and 23 and the lines 25 and 10, as shown in FIG. 4, so that the liquid nitrogen circulates in an opposite direction to that of the natural gas and produces the cooling of all the heat exchangers 51, 18 and 5 in succession.

This implementation is particularly advantageous for working offshore. The plant shown in FIG. 4 may be arranged on a platform, on account of its low weight and its small bulk. A tanker can deliver the liquid nitrogen required for operating the plant and leave with the liquefied natural gas.

The optional devices for liquid hydrocarbon removal have not been shown in this plant, since these devices are of a conventional type.

The process of purification according to FIG. 3 may be illustrated with the aid of the following example in which the concentrations are expressed in weight fractions (% or p.p.m.). Natural gas containing 0.089% of water, 0.965% of carbon dioxide and 7.45% of hydrogen sulphide is supplied to delivery line 46 at a pressure of $4.2 \times 10^6$ Pa and a temperature of 25° C., at a weight flow rate of 36 tonnes/hour. The part of this natural gas, which after having passed through the membrane 44 of separator 43 leaves by the discharge line 49, contains 0.83% of water, 4.95% of carbon dioxide and 54.3% of hydrogen sulphide. It is at a temperature of 25° C. and a pressure of $0.15 \times 10^6$ Pa and its flow rate is 3 tonnes/hour. The main stream of natural gas leaving at line 47 from the gaseous permeation separator 43 contains 0.0147% of water, 0.74% of carbon dioxide and 2.54% of hydrogen sulphide. Its temperature is 25° C., its pressure is $4 \times 10^6$ Pa and its weight flowrate is 33 tonnes/hour.

At the injection point 4, the natural gas stream receives via the line 7 methanol containing 1.5 p.p.m. of water, 89 p.p.m. of carbon dioxide and 46 p.p.m. of hydrogen sulphide. After being cooled to $-60°$ C. in the heat exchanger 5, the liquid phase leaving via the line 15 contains 16 p.p.m. of water, 0.082% of carbon dioxide and 0.28% of hydrogen sulphide.

The gaseous phase leaving via the line 14 receives at the injection point 20 a flow of 300 tonnes/hour of new and/or regenerated methanol. After cooling to $-80°$ C. in the heat exchanger 18, there is obtained in line 27 a purified natural gas which now only contains 0.6 p.p.m. of water, 50 p.p.m. of carbon dioxide and 2.8 p.p.m. of hydrogen sulphide.

Naturally, this example is given by way of illustration only of one of the possible embodiments of the process according to the invention. Numerous alternative forms and modifications can, moreover, be introduced into the systems shown in the drawings, without departing from the scope of the invention.

There is thus provided a simple process for purifying natural gas, which is capable of being integrated particularly into a liquefaction process and capable, if appropriate, of being employed on an offshore platform. Additionally, the consumption of solvent in a particular solvent-type process for purifying natural gas can be reduced.

What is claimed is:

1. In a process for purifying a natural gas containing undesirable components of at least water or carbon dioxide or hydrogen sulfide comprising; injecting methanol into said natural gas, lowering the temperature of said mixture of natural gas and methanol thus produced to a temperature, called the absorption temperature, at which an absorption of the undesirable components present in said natural gas by the methanol is produced, and separating the natural gas thus purified from said methanol phase which has absorbed said undesirable components, the improvement comprising; subjecting said natural gas to be purified to a succession of purification stages each of said stages having an outlet and as separator thereat, in each stage injecting methanol into said natural gas; the mixture of said natural gas and said methanol thus produced subjected to said absorption temperature and said natural gas is separated and withdrawn from said methanol phase at an upper portion of said separator, a liquid phase formed by hydrocarbons which have condensed withdrawn from an intermediate portion of said separator and spent methanol is withdrawn from a lower portion of said separator, wherein the partially purified natural gas which leaves a stage other than the last of said stages enters the next stage which follows it with purified natural gas being obtained at the outlet of said last stage, said methanol injected into said natural gas in any of said stages other than said last stage is separated at the outlet following said stage, and at least a part of the methanol at the outlet of the first of said stages being regenerated by removing at least a part of said undesirable components which it has absorbed and at least a part of the methanol regenerated in this way is injected into said last stage, wherein, methanol containing a weight proportion of water of between 5 and 50% is injected into said natural gas in said last stage.

2. A process according to claim 1, comprising; subjecting said natural gas to be purified to a preliminary purification by permeation upstream of the first stage of said succession of purification stages.

3. A process according to claim 1, comprising regenerating methanol withdrawn at the outlet of said first stage in two successive steps comprising a first step for separating at least a part of any acid gases present and a second step of separating water, said second step being carried out only on a fraction below 20% of the total flow of said withdrawn methanol.

4. A process according to claim 1 associated with a liquefaction process, wherein said purified natural gas obtained in said last stage of said purification process is supplied to a final heat exchanger causing liquefaction of said natural gas by means of liquid nitrogen.

5. A process according to claim 4, wherein a stream of liquid nitrogen is introduced into said final heat exchanger and circulates from one of said stages to another of said purification stages in a direction opposite to the direction of flow of said natural gas.

* * * * *